Figure 3:
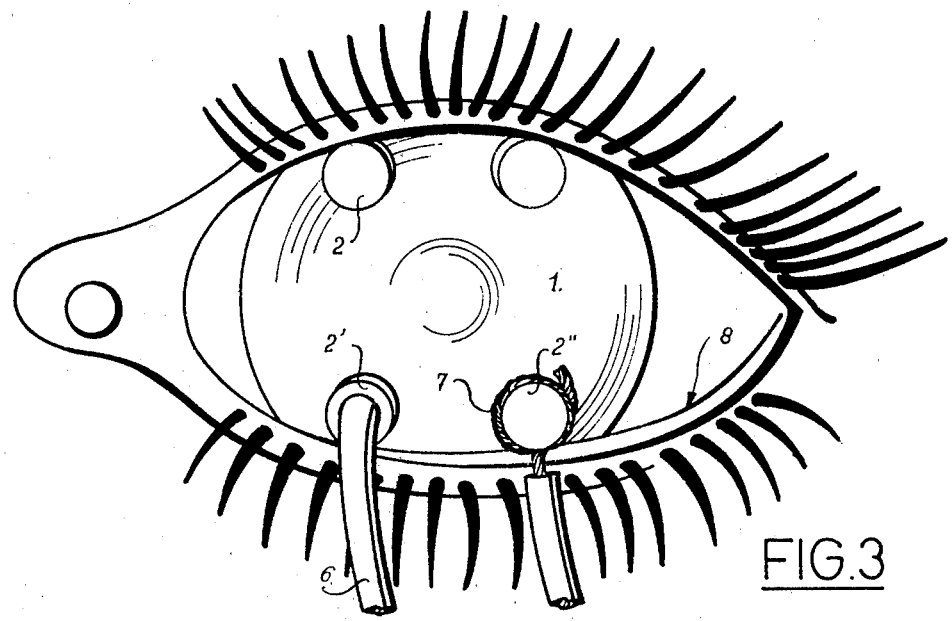

United States Patent [19]

Grounauer

[11] 4,386,831
[45] Jun. 7, 1983

[54] DEVICE FOR THE MEASUREMENT OF ELECTRICAL POTENTIALS OF THE EYE

[76] Inventor: Pierre-Alain Grounauer, Rue de l'Ale 38, 1003 Lausanne, Switzerland

[21] Appl. No.: 237,737

[22] Filed: Feb. 24, 1981

[30] Foreign Application Priority Data

Mar. 14, 1980 [CH] Switzerland ............... 2009/80

[51] Int. Cl.³ .............. A61B 3/10; G02C 7/04
[52] U.S. Cl. .................. 351/205; 351/221; 351/160 R
[58] Field of Search .............. 351/160, 6, 16; 128/733, 734, 745

[56] References Cited

U.S. PATENT DOCUMENTS 4,109,648  8/1978  Larke et al.
4,169,664  10/1979  Baily .................. 351/160 R

FOREIGN PATENT DOCUMENTS 431950  11/1925  Fed. Rep. of Germany.
865935  12/1952  Fed. Rep. of Germany.
2639635  3/1978  Fed. Rep. of Germany.
7834144  7/1980  France.

OTHER PUBLICATIONS

IEEE Transactions on Biomedical Engineering, vol. BME 22, No. 5, Sep. 1975, A. Troelstra et al.: "The Electrical Response of the Human Eye to Sinusoidal Light Stimulation," pp. 369-378.

Primary Examiner—John K. Corbin
Assistant Examiner—Rodney B. Bovernick
Attorney, Agent, or Firm—Young & Thompson

[57] ABSTRACT

A corneal lens (1) is provided with a measurement electrode (4), a portion of which being flush with the concave surface of the lens or protruding from said surface, in such a manner to be in service position directly in contact with the cornea of the eye. The convex surface of the lens comprises pins (2) to maintain open the eyelids.

This device allows to obtain without any inconvenient for the subject an electroretinogram usable for the ophthalmologist's diagnostic.

9 Claims, 4 Drawing Figures

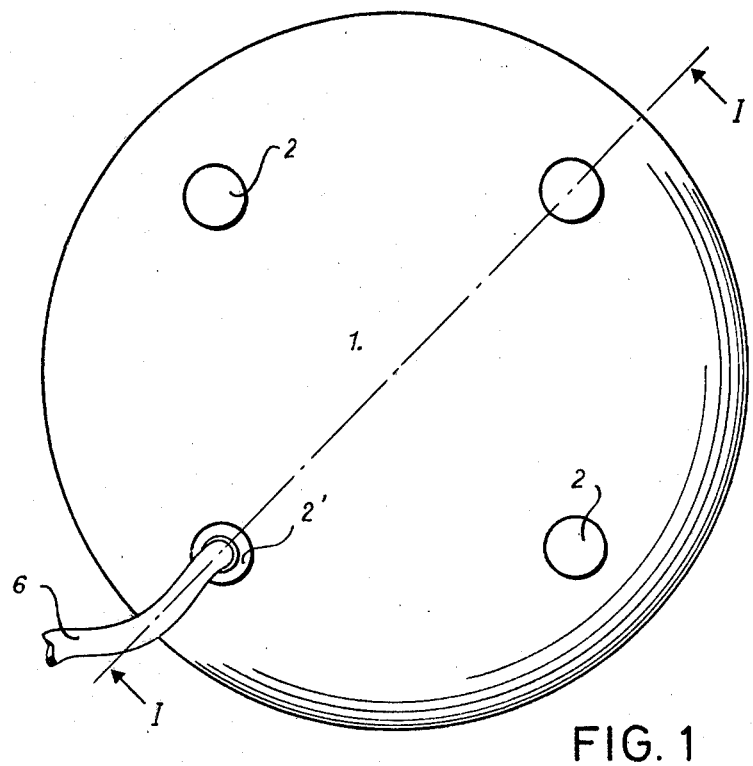
FIG. 1
FIG. 2
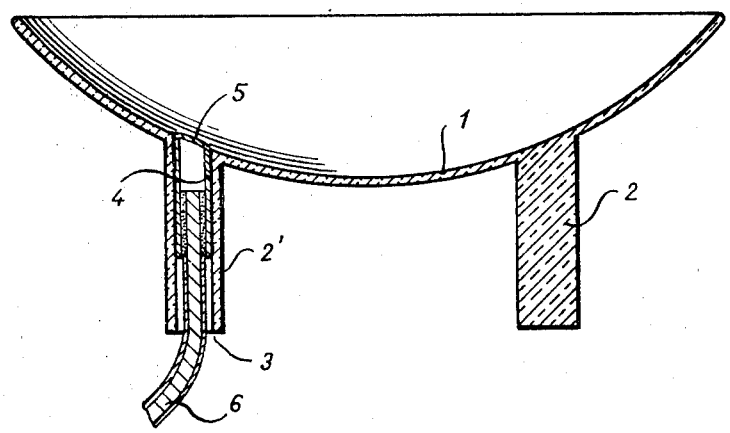

DEVICE FOR THE MEASUREMENT OF ELECTRICAL POTENTIALS OF THE EYE

The present invention relates to a device for the measurement of electrical potentials appearing on the cornea of the human or animal eye in response to a light stimulation of said eye and so as to establish an electroretinogram (ERG).

It is known that light stimulation of human or animal eye modifyes the electrical behaviour of the photoreceiving cells. After a suitable photostimulation, it is thus possible to measure, in normal or pathological conditions, these electrical characteristics, of which the study allows, in ophthalmological medicine, to know for example if the subject is seeing or not (examinations realized on new-born children or animals) or if the retina is still in good condition (pre-operatory statement). In order to collect these electrical characteristics, the electrical potentials should be measured by means of an electrode applied directly onto the cornea of the eye, then the signals received are amplified and recorded graphically or visualized on a cathodic screen as a function of the time.

Devices are already known with a measurement electrode to be put in electrical contact with the eyeball. However, these devices now used present the following disadvantages:

they are heavy and combersome, which constitutes an important drawback for the examinations made on the new-born and the children as well as an uncomfortable characteristic for the examinations on the adults;

the measurement electrode is not directly in contact with the cornea of the eye, which necessitates the presence between the eye and the electrode of an electrically conducting liquid, which should in no circumstances contain air bubbles, this being difficult to obtain in a constant manner;

due to their relative complexity, these devices are relatively costly and are intended to be used several times; nevertheless it is difficult to sterilize them quickly and easily between two measurements, and their repeated use thus presents non negligible risks of contamination.

Therefore, the purpose of the present invention consists in providing a device for the measurement of electrical potentials appearing on the cornea of the human or animal eye in response to a light stimulation of said eye so as to establish an electroretinogram, which obviates to the above mentioned drawbacks, and more particularly which is simple, light, little cumbersome, cheap, easily sterilizable and in principle intended for only one simple use.

The device object of this invention which leads to reach the above purpose comprises a corneal lens provided with a measurement electrode, at least a portion of said electrode being flush with the concave surface of the lens or protruding from said surface so as to be in service position directly in contact with the cornea of the eye, and the convex surface of the lens comprising means for maintaining in service position the eyelids opened.

The annexed drawings illustrate schematically and by way of example embodiments of the device according to the invention.

Figure 4:
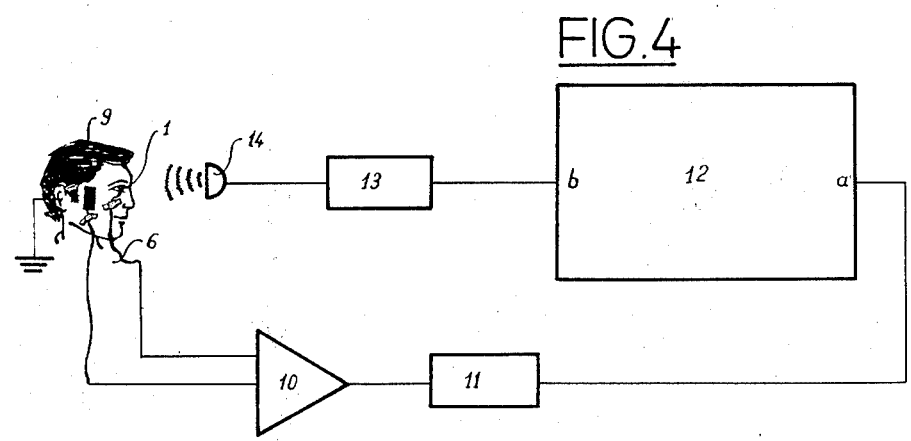

FIG. 1 is a top view of a first embodiment, and
FIG. 2 is a section view along the line I—I of FIG. 1.
FIG. 3 is a view of a second embodiment in service position on the cornea of an eye.
FIG. 4 is a bloc scheme of an apparatus for establishing an electroretinogram.

Referring to FIGS. 1 and 2, the device comprises a contact lens 1 of the conventional type made of a chemically and optically neutral transparent plastic material, the radius of curvature of which being suitable for a good contact with the cornea of an eye.

The convex surface of the lens 1 is provided with four pins 2, also made of plastic material, and which serve as blepharostats, that is as means for maintaining the eyelids open when the lens is in service position on the cornea. One of these pins 2 is provided with an axial boring 3. The four pins 2 are generally made of manufacture together with the lens by injection of plastic material.

A small metallic rod or tube 4 intended to serve as measurement electrode is driven into the boring 3 of the pin 2', in such a manner that the closed end 5 of said tube 4 be slightly protruding from the concave surface of the lens 1. The protruding portion 5 of the electrode 4 is rounded so that it does not risk to hurt the cornea when the lens is in service position on the eye.

A contact wire 6 is linked, for example by welding, with the electrode 4, and connects this latter to an apparatus for measuring the electrical potentials, which amplify and transmit the signals received to a graphic recorder or to a cathodic screen.

The measuring electrode can also be constituted of a ring fixed to the concave surface of the lens. However, this electrode is preferably constituted by a conductor coating partly or completely covering the concave surface of the lens, and the contact wire with this coating serving as electrode emerging as previously from the lens through a boring provided in one of the pins. This conductor coating can be obtained in a known manner for example by vacuum metallization or chemical vapor deposition (CVD).

The electrode must be neutral, without any photoelectrical effect and non polarizable, in order to avoid any risk of electrochemical reaction. It is thus generally made of a noble metal such as gold or silver, or at least coated with such a metal.

In order to obtain an electroretinogram, it is necessary, in addition to the measuring electrode, to have an inactive or reference electrode as well as a ground electrode, which can be fixed for example for the examination on the homolateral ear or the temple and on the forehead, respectively. In the embodiment of the device according to the invention shown on FIG. 3, the inactive or reference electrode is constituted by a conducting wire 7 attached around one of the pins 2", being preferably not that through which the contact wire 6 of the measuring electrode passes. In the service position illustrated, the lens 1 being disposed on the globe of the eye, the inactive or reference electrode 7 is into contact with the lower eyelid 8.

Generally, the contact wire 6 of the measuring electrode as well as the conducting wire 7 constituting the inactive or reference electrode are preferably shielded so as to decrease the formation of parasitic effects which could disturb the signals collected. Furthermore, the free end of these wires can be provided with a plug suitable for being directly introduced into the corresponding input of the apparatus to which they are to be connected.

FIG. 4 illustrates a simplified bloc scheme showing how an electroretinogram can be obtained. The lens 1 is disposed on the eye of the subject 9 to examine and the contact wire 6 of the measuring electrode is connected to a physiological amplifier 10, as well as an inactive or reference electrode attached for example on the temple of said subject. The measurement apparatus also comprises a band pass filter 11 connected to the output of the amplifier 10 and serving to optimalize the signal/-noise ratio, prior to reach a signal averager 12. This latter comprises on one part a graphic recorder or a cathodic screen (a) for collecting and visualizing the signals issued from the filter 11 and on the other part a control device of the light stimulations (b). The light stimulations are furnished by a stimulator comprising a control and regulating unit 13 and a light source 14 directed towards the eye(s) of the subject 9. The principle and the working of the apparatus are described in more details in the publication "Introduction to evoked potential instrumentation" of Nicolet Instruments Co. (Madison, Wisc., USA / Mar. 1, 1979).

The light stimulation can be continious or discontinious. In the first case, a sinusoidal light frequence can be superimposed, for example as described by V. V. Toi and P. A. Grounauer in Rev. Sci. Instrum. 49(10), 1403–1406, 1978. In the second case, the light source can be constituted by an electronic flash for the examination of the whole eye or by a punctual source for the examination of only a determined portion of the eye. A stimulator of the type described by V. V. Toi and P. A. Grounauer in Klin. Mbl. Augenheilk. 176(4), 530–532, 1980 can be used.

With regards to the known devices, the device according to the present invention presents the advantage that it is constituted by a corneal lens, and thereby that it is light and easily bearable by the examined subject, even if it is a child. This lens can also have a maximal transparency of the whole visible spectra and thus have a neutral optical power which does not modify the visual accuity.

Furthermore, the electrode of measurement being directly in contact with the cornea of the eye, it is not necessary to have a conductor contact liquid between the electrode and the eye.

Finally, this device being simple and easy to manufacture, it is of a very low cost and can be consequently sold under a non reusable and disposable form, this avoiding any risk of contamination from a patient to another one. For example, the corneal lens with measurement electrode can be commercialized under sealed packing and after sterilization according to a known method by radioactive treatment under packing. Thus, the ophthalmologist can realize examinations by measuring of electrical potentials directly on the cornea of the eye by using for each examined subject a new lens which will be taken out of its sterile packing only at the last moment and which will be thrown after the measurement.

What is claimed is:

1. A device for the measurement of electrical potentials appearing on the cornea of the human or aninal eye in response to a light stimulation of said eye and so as to establish an electroretinogram (ERG), which consists in a corneal lens provided with a measurement electrode, at least a portion of said electrode being flush with the concave surface of the lens or protruding from said surface so as to be in service position directly in contact with the cornea of the eye, and the convex surface of the lens comprising means for maintaining in service position the eyelids opened.

2. A device according to claim 1 in which the electrode is constituted by a rod, an end of which being in service position in contact with the cornea of the eye.

3. A device according to claim 1 in which the electrode is constituted by a ring attached to the concave surface of the lens.

4. A device according to claim 1 in which the electrode is constituted by a coating covering partly or completely the concave surface of the lens.

5. A device according to one of claims 1 in which the electrode is made of a non polarizable metallic material.

6. A device according to claim 1 in which the means for maintaining open the eyelids are constituted by pins disposed on the convex surface of the lens.

7. A device according to claim 6 in which a contact wire connecting the electrode to a measuring apparatus passes through an axial boring in one of the pins.

8. A device according to claims 6 in which the corneal lens and the pins are made of one piece of manufacture by injection of plastic material.

9. A device according to claim 7 in which a conductor wire is attached to a pin, which is not that through which the electrode of measurement passes, said wire serving in service position as inactive or reference electrode.

* * * * *